United States Patent [19]

Cohen et al.

[11] 4,179,497

[45] Dec. 18, 1979

[54] SOLID STATE OPHTHALMIC MEDICATION

[75] Inventors: Edward M. Cohen, Beaumont, France; Wayne M. Grim, Doylestown, Pa.; Richard J. Harwood, Philadelphia, Pa.; Gunvant N. Mehta, Lansdale, Pa.

[73] Assignee: Merck & Co., Inc., Rahway, N.J.

[21] Appl. No.: 959,550

[22] Filed: Nov. 13, 1978

Related U.S. Application Data

[63] Continuation-in-part of Ser. No. 553,399, Feb. 26, 1975, abandoned, which is a continuation-in-part of Ser. No. 519,323, Oct. 31, 1974, abandoned, which is a continuation-in-part of Ser. No. 425,426, Dec. 17, 1973, abandoned.

[51] Int. Cl.$^2$ .......................... A61K 9/22; A61K 9/26
[52] U.S. Cl. .................................... 424/22; 128/260; 424/14; 424/16; 424/19; 424/35; 424/362
[58] Field of Search .................... 128/260; 424/14–22, 424/35, 362

[56] References Cited

U.S. PATENT DOCUMENTS

| 108,034 | 10/1870 | Kraus | 424/360 |
|---|---|---|---|
| 273,410 | 3/1883 | Wadleigh | 128/271 |
| 1,872,826 | 8/1932 | Schulemann et al. | 260/286 AR |
| 2,397,903 | 4/1946 | Puetzer | 260/251 |
| 3,278,521 | 10/1966 | Klug | 260/231 |
| 3,424,842 | 1/1969 | Nurnberg | 424/94 |
| 3,450,814 | 6/1969 | Bechtold et al. | 424/180 |
| 3,776,001 | 12/1973 | Hanke et al. | 128/271 |
| 3,845,201 | 10/1974 | Haddad et al. | 424/19 |
| 3,852,421 | 12/1974 | Kuyanagi et al. | 424/94 |
| 3,863,633 | 2/1975 | Ryde et al. | 128/260 |
| 3,867,519 | 2/1975 | Michaels | 424/19 |
| 3,868,445 | 2/1975 | Ryde et al. | 424/14 |
| 3,870,791 | 3/1975 | Haddad et al. | 424/22 |
| 3,875,300 | 4/1975 | Homm et al. | 424/28 |
| 3,981,303 | 9/1976 | Higuchi et al. | 128/260 |
| 3,986,510 | 10/1976 | Higuchi et al. | 128/260 |
| 3,993,071 | 11/1976 | Higuchi et al. | 128/260 |
| 4,001,388 | 1/1977 | Shell | 424/14 |

FOREIGN PATENT DOCUMENTS 1090492 11/1967 United Kingdom.
1324191 7/1973 United Kingdom.
1362700 8/1974 United Kingdom.

OTHER PUBLICATIONS

Hercules, Inc., "Fact Sheet on Klucel", 2 pp., Dec. 4, 1972.
Hercules, Inc., "Klucel Hydroxypropyl Cellulose", 32 pp., (1971).
Klug, J. Polymer Sci., Part C, No. 36:491–508 (1971), "Some Properties of Water–Soluble Hydroxyalkyl Celluloses and Their Derivatives".
Lemp et al., Ann. Ophthalmol. 4(1):15–20, (1972), "Ophthalmic Polymers as Ocular Wetting Agents".
Lemp, "Artificial Tear Solutions", Int. Ophthal. Clin. 13(1):221–228 (1973).
U.S.P.T.O. Translation, (22 p.), 10/17/78, (P.C.C.), of Saias et al., Ann. Pharm. Fr., 27:557–570 (1969), The Pamoates: A Class of Oral and Prolonged Action Drugs.
Anon, Chem. Abstr. 14, #3501$^6$ (1920), of Rep. Lab. Am. Med. Ass., 12:96–97 (1919), "The Relative Permancy in Moist Air of Pilocarpine Hydrochloride and Pilocarpine Nitrate".
Loucas et al., J. Pharm. Sci., 61(6):985–986, Jun. 1972, "Solid State Ophthalmic Dosage Systems".
British Pharmacopoeia (1953), Pharmaceutical Press, London (1953), pp. 59, 60, 155, 263, 300, 428, 876.
"P.F.", vol. I, Pharmaceutical Formulas, 10th Ed. Chemist and Druggist, London, (1946), pp. 279–280, 977, 1117.
Prosser, James, A Guide to the New Pharmacopoeia, 2nd Ed. Churchill, London (1885), pp. 7, 66–69, 72–75, 94–95, 110–111, 116.

*Primary Examiner*—Shep K. Rose
*Attorney, Agent, or Firm*—Edmunde D. Riedl; Mario A. Monaco

[57] ABSTRACT

Solid unit dosage medicaments which are suitable for use in animals and humans are prepared with hydroxypropyl cellulose as the primary formulating excipient. These medicaments are particularly suitable for ophthalmic use since they are slowly but completely water soluble when they are inserted in the cul-de-sac of the eye and thus provide for a convenient means of prolonged treatment of the eye with concomitant reduced dosing frequency.

1 Claim, No Drawings

SOLID STATE OPHTHALMIC MEDICATION

RELATED CASES

This application is a continuation-in-part of U.S. Ser. No. 553,399 filed Feb. 26, 1975, which is a continuation-in-part of U.S. Ser. No. 519,323 filed Oct. 31, 1974, which is a continuation-in-part of U.S. Ser. No. 425,426 filed Dec. 17, 1973, all now abandoned.

This invention relates to the preparation of solid medicinal products suitable for use in animals and humans. More particularly, it is concerned with solid unit dosage forms of therapeutically active substances and hydroxypropyl cellulose. Specifically, it is concerned with solid dosage forms or ophthalmic inserts comprising hydroxypropyl cellulose and medicinal agents which can be used in the treatment of the eye with a minimum of interference of vision.

The usual treatment of various eye conditions consists of applying doses of appropriate medicaments in aqueous suspension solutions or ointments. While such treatments are satisfactory for treating eye conditions where only one or several applications of the medicinal agents are necessary, certain eye conditions require more frequent doses and the treatment is inconvenient to the patient. Recently, it has been proposed to apply the ophthalmic active medicinal agents in a solid form on a inert matrix (e.g. U.S. Pat. No. 3,710,795). This method has the disadvantage that the inert matrix must be removed after the drug has been completely released from the matrix. More recently, Loucas et al. [J. of Pharm. Sci., Vol. 61, page 985 (June 1972)] found that the alginic acid salt of pilocarpine when administered as a solid state opthalmic insert provides a greater miotic response than could be obtained by the administration of conventional pilocarpine solutions in the rabbit eye.

It is an object of this invention to provide improved ophthalmic inserts providing prolonged activity and minimizing the frequency of doses necessary in the treatment of various eye conditions. It is a further object to provide a drug-containing ophthalmic insert providing a slow but continuing uptake of the medicament in the lacrimal fluid and providing minimum loss of the drug into the nasolacrimal ducts. Another object is to provide an ophthalmic insert which, when administered in the cul-de-sac of the eye, completely dissolves in the lacrimal fluid and thereby avoids the need for removing any drug depleted material. Other objects will be apparent from the detailed description of our invention hereinafter provided.

In accordance with our invention, these desiderata are achieved with ophthalmic inserts comprising hydroxypropyl cellulose and an ophthalmic medicament wherein the medicament is uniformly dispersed in the heterogeneous system comprising a medicament in the hydroxypropyl cellulose matrix. Suitable inserts which can be prepared in various ways as will hereinafter be described produce ophthalmic preparations having prolonged activity on administration. Egress of the drug from the ophthalmic insert is accomplished by the gelation and finally by the dissolution of the matrix in the lacrimal fluid, thereby eliminating any need to remove the drug depleted matrix before administering a further dose.

Hydroxypropyl cellulose is a non-ionic water soluble cellulose ether having properties which are uniquely suitable for use in the preparation of ophthalmic inserts. Thus, it is water soluble and hence dissolves in the aqueous lacrimal fluids. In addition, it is thermoplastic and can therefore be advantageously combined with the ophthalmic drug using conventional plastic processing procedures such as compression molding, injection molding and extrusion prior to unit dose subdivision. Hydroxypropyl cellulose is available in several polymeric forms, all of which are suitable in the preparation of the ophthalmic inserts of the present invention. Thus, the products sold by Hercules Incorporated of Wilmington, Delaware under the name KLUCEL such as KLUCEL HF, HWF, MF, GF, JF, LF, and EF which are intended for food or pharmaceutical use are particularly useful in preparing the new inserts of our invention.

The compositions of this invention can be prepared by various methods. Thus, the drug and the hydroxypropyl cellulose can be dissolved in a suitable solvent and the solution evaporated to afford a thin film comprising the hydroxypropyl cellulose and the drug which can then be subdivided to prepare suitable inserts containing the desired amount of the medicament. Alternatively, and in accordance with a preferred embodiment of our invention, we find that the inserts can be prepared most conveniently using the thermoplastic properties of the hydroxypropoyl cellulose. For example, the medicament and the hydroxypropyl cellulose can be warmed together at temperatures between about 150° F. and 400° F. and the resulting mixture molded to form a thin film. It is generally preferred to prepare the inserts by molding or extrusion in accordance with procedures which are well known in the art. The molded or extruded product can then be subdivided to afford inserts of suitable size for administration in the eye. For example, castings or compression molded films having a thickness of about 0.5 mm. to 1.5 mm. can be subdivided to obtain suitable inserts in the form of squares, rectangles, circles, semi-circles, and the like containing the desired amount of active ingredient. Rectangular segments of the cast or compressed film having a thickness between about 0.5 and 1.5 mm. can be cut to afford shapes such as rectangular plates of 4×5–15 mm. or ovals of comparable size. Similarly, extruded rods having a diameter between about 0.5 and 1.5 mm. can be cut into suitable sections to provide the desired dosage of medicament. For example, rods of 1.0 to 1.5 mm. in diameter and about 10 mm. long are found to be satisfactory. The inserts may also be directly formed by injection molding. All of the ophthalmic inserts prepared in accordance with the present invention should be formed so that they do not have any sharp edges or corners which could cause damage to the eye.

The ocular inserts prepared in accordance with this invention can also contain plasticizers to make the ophthalmic inserts more pliable. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from about 0% to about 30% by weight. A particularly preferred plasticizer is water which is present in amounts of at least about 5% and more preferably at least about 10%. In actual practice, a water content of from about 10% to about 20% is preferred since it may be easily accomplished and adds the desired softness and pliability to the insert.

When plasticizing the solid medicinal product with water, the medicinal product is contacted with air having a relative humidity of at least about 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable drugs which can be administered by the inserts of the present invention that might be mentioned are antibacterial substances such as β-lactam antibiotics, tetracyclines, chloramphenicol, neomycin, gramicidin, bacitracin, sulfonamides; aminoglycoside antibiotics such as gentamycin, kanamycin, amikacin, sisomicin; and tobramycin; nitrofurazones, and the like; antihistaminics and decongestants such as pyrilamine, chlorpheniramine, tetrahydrazoline, antazoline, and the like; antiinflammatories such as cortisone, hydrocortisone, betamethasone, dexamethasone, fluocortolone, prednisolone, triamcinolone, indomethacin, Clinoril its salts and its corresponding sulfide, and the like; miotics and anticholinesterases such as echothiophate, pilocarpine, physostigmine salicylate, diisopropylfluorophosphate, and the like; mydriatics such as atropine, homatropine, scopolamine, hydroxyamphetamine, and the like; and other medicaments used in the treatment of eye 3-morpholino-4-(3-t-butylamino-2-hydroxypropoxy)-1,2,5-thiadiazole, i.e., Timolol especially as the hydrogen maleate salt.

These drugs or derivatives thereof such as salts, covalent derivatives, for example, esters or amides, or other therapeuticaly active forms can be admixed with the hydroxypropyl cellulose in the form of the water soluble inserts prepared as described above for the treatment of various eye diseases. These forms are especially advantageous for the treatment of conditions where prolonged drug administration is indicated, for example, in eye diseases or eye disorders such as uveitis, glaucoma, diseases of the cornea such as, for example, purulent keratitis, herpes simplex keratitis, herpes zoster, acne rosacea, interstitial keratitis, and the like, diseases of the orbit such as exophthalmos and periostitis and diseases of the conjunctive such as mucopurulent conjunctivitis and ophthalmia. Also, this method of the administration of ophthalmic active drugs can be used when post-operative treatment is needed after retinal or cataract surgery. A drug which is of particular use as described above is pilocarpine pamoate.

The method of administering drugs as a water soluble insert is especially useful in the administration of pilocarpine to treat glaucoma, a condition characterized by an increase in intraocular pressure. The present treatment of this condition involves the use of solutions of pilocarpine acid salts which are administered to the eye in the form of drops at frequent intervals. By inserting the opthalmic inserts of the present invention, a miotic response of up to 9–10 hours may be obtained in rabbits compared to the short response of 2–4 hours obtained by the administration of drops. The pilocarpine can be administered preferably in the form of acid salts of this drug such as the hydrochloride, alginate, pamoate, and the like. The ophthalmic inserts of the present invention can contain up to about 35% by weight of pilocarpine to afford a dose of about 1–6 mgs. of pilocarpine per insert.

In general the ophthalmic inserts of the present invention will contain from about 0.1 to about 35% of the medicament, from about 65 to about 99.9% of hydroxypropyl cellulose and from 0 to about 30% of plasticizer, preferably water. In special situations, however, the amounts may be varied to increase or decrease the dosage schedule. If desired, the insert may also contain in addition to the plasticizers, buffering agents and preservatives. Suitable water soluble preservatives which may be employed in the insert are sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from 0.001 to 5% by weight of solid insert, and preferably 0.1 to 2%. Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer.

The inserts as is well known, can be prepared to dissolve in any given length of time, and accordingly the drug as well, by merely adjusting the size and weight of the insert, the molecular weight of the polymer and/or by the use of other agents such as plactizers. Typically for an insert which contains approximately 10% by weight of water and about 15–35% by weight of drug such as indomethacin and pilocarpine pamoate, and is from about 8–12 mg. in weight. The dissolution rate is from about 0.5 mg./hr. to about 3 mg./hr. Suitably, however, the dissolution rate may be from about 0.004 mg./hr. up to about 20 mg./hr. but preferably is from about 0.04 mg./hr. to about 4.0 mg./hr. and especially from about 0.08 mg./hr. to about 3.0 mg./hr.

The following examples describe specific methods of preparing the novel ophthalmic inserts of our invention and are provided to illustrate specific embodiments of our invention.

EXAMPLE 1

The following aqueous solutions were prepared

| Solution A | |
|---|---|
| Pilocarpine base | 2.08 g. |
| Alginic acid | 2.42 g. |
| Hydroxypropyl cellulose (KLUCEL GF) | 0.45 g. |
| Water | 30 ml. |
| Solution B | |
| Pilocarpine base | 2.08 g. |
| Alginic acid | 2.42 g. |
| Hydroxypropyl cellulose (KLUCEL HF) | 0.45 g. |
| Water | 30 ml. |
| Solution C | |
| Pilocarpine base | 2.08 g. |
| Alginic acid | 2.42 g. |
| Hydroxypropyl cellulose (KLUCEL JF) | 0.45 g. |
| Water | 30 ml. |

Thin films were prepared by casting films from these solutions and then cutting the dried films into rectangular shapes, approximately 3 by 10 mm. The in vivo disappearance time and the total miotic action of these ophthalmic inserts were determined as follows:

Randomized series of six male and female New Zealand albino rabbits weighing 3–3.5 kg., approximately 4–5 months of age, were used. The animals were kept in restraint boxes in a room with a steady light of weak intensity. The naive animals were accustomed to the experimental conditions (laboratory, restraint boxes ...) once before time of testing. The same rabbits were re-used with at least 14 days rest between two testings; they were finally eliminated after five times. The animals were accustomed to the environment for 1 hour, and after initial measurements, the compounds to be studied were administered (solutions, rods, discs, ointment ...) into the conjunctival sac of one eye and the other non-treated eye was the control. The pupil measurements were made 5, 30, 90, 210 and 360 minutes after treatment. The average pupil diameters and confidence limits for $P \leq 0.05$ of each series (6 rabbits) were given. The pupil diameter was measured with a LU-NEAU and COFFIGNON pupillometer whose principle of operation consists in superimposing the virtual image of a red light beam of variable diameter into the plane of the iris. With an adjustable diaphragm, one adjusts the diameter of the bundle of red light rays to coincide with that of the pupil. The diameter of the diaphragm is recorded directly in millimeters. The results of these tests are shown in the following tables:

| Preparation No. | Disappearance Time (minutes) | Mg. of Pilocarpine per Insert | Total Miotic Activity* Insert/ Total Miotic Activity* Solution |
| --- | --- | --- | --- |
| A | 10<t<30 | 4.01 | $\frac{23}{20.7} = 1.11$ |
| B | 120<t<240 | 4.56 | $\frac{26.3}{16.8} = 1.56**$ |
| C | 240<t<300 | 5.77 | $\frac{34.1}{16.4} = 2.08**$ |

*Total miotic activity is an equivalent term for total biological response and is expressed as the area under the curve representing pupil size change from the time the dose was administered to the time for the pupil size to return to the control diameter. The area of the response curve is obtained from a plot of the pupil size versus time for the treated eye versus the control eye.
**Effect is significantly better than solution after 210 minutes.

EXAMPLE 2

A. Preparation of pamoic acid salt of pilocarpine

The pilocarpine base 20.7 g. is dissolved in 20 ml. of water and a stoichiometric amount 19.3 g. of pamoic acid is added. The mixture is stirred for about 3 hours until a homogenous brown oily mixture results. The mixture is placed in a heated (50°–60° C.) vacuum (22 in. Hg.) desiccator. Each day, the container is removed from the desiccator and the portion of the oil which has dried on the surface is removed and ground to a powder. The container with the remaining liquid oily mixture is again placed in the heated vacuum desiccator. This is repeated until all of the oil is dried and removed from the container giving a yield of over 90%. The analytical data is as follows:

(1) Moisture—3.15% K.F.
(2) Elemental Analysis

|   | Calc., % | Experimental, % | Calc. %, corrected for moisture |
| --- | --- | --- | --- |
| N | 6.98 | 6.8, 7.14 (2 runs) | 6.76 |
| C | 67.31 | 64.75, 65.01 (2 runs) | 65.19 |
| H | 5.77 | 6.17, 6.15 (2 runs) | 5.95 |

A mixture of 25 g. of 60 mesh pilocarpine pamoate and 75 g. of 60 mesh hydroxypropyl cellulose (KLUCEL HF) are mixed thoroughly using conventional dry powder mixing procedures such as mortar and pestal, twin shell blender, planetary mixer, and the like. The mixture is then passed through a 30 mesh screen and remixed. A small amount (2 to 5 g.) of the mixture is then placed in the center of a clean dry aluminum sheet having a thickness of 0.2755 in., the surface of which is coated with a lubricant such as aerosolized lecithin and a thickness regulator (shim) of about 1 mm. is placed in each of the four corners of the aluminum sheet. A second lubricated 0.2755 in. thick aluminum sheet is placed over the first sheet and transferred to a hydraulic press, such as a Model B Carver Press, between two 6×6 in. platens equipped for heating and cooling; the top and bottom platens having been previously preheated to a temperature of 200° F. The press is then closed and the material subjected to a pressure of 10,000 lbs. gauge while maintaining the platens at the same temperature. After 1 minute, cold water is circulated in the platens to cool the product while the pressure is being maintained. After about 2 minutes, the pressure is released and the product in the form of a wafer-thin sheet is removed. It is then cut into small rectangles approximately 10 mm. by 4 mm. having a thickness of about 0.8 mm. and containing about 2 to 4 mg. of pilocarpine per unit dose.

The ophthalmic inserts so obtained were tested for miotic activity in rabbits using the procedures described in Example 1. At the same time, a conventional solution of pilocarpine comprising an equivalent dose of pilocarpine was administered to one group of rabbits. The results of these tests are shown in the following table:

|   | Mean Pupil Diameters - mm. | | |
| --- | --- | --- | --- |
| Time (hrs.) | Control | Conventional Pilocarpine Solution | Rectangular Pilocarpine Pamoate Inserts |
| 0 | 7.5 | | |
| ½ | 7.3 | 5.2 | 5.2 |
| 1½ | 7.3 | 5.6 | 4.8 |
| 3½ | 7.4 | 6.7 | 5.0 |
| 6 | 7.5 | 7.4 | 5.5 |
| 7 | 7.4 | — | 5.7 |
| 8 | 7.4 | — | 5.6 |
| 9 | 7.4 | — | 6.3 |
| 10 | 7.4 | — | 6.8 |

The above table shows the prolonged miotic effect obtained when the pilocarpine is administered in the form of the rectangular insert formed with the hydroxypropyl cellulose.

The above ophthalmic inserts are placed in a cabinet and contacted for 2 days with air at room temperature and a relative humidity of 88%. The ophthalmic inserts having an initial weight of about 18 mgs. increase to a weight of 20 mgs. in the two-day period showing a pickup of 2 mgs. of water or about 11% based on the total weight of the insert. The plasticizing effect of the water makes the insert much softer and pliable.

EXAMPLE 3

The mixture of pilocarpine pamoate and hydroxypropyl cellulose prepared as described in Example 2 is used for the preparation of an extruded filament in conventional extrusion equipment in the following manner.

The heater control of a Custom Scientific Instrument Mini-Max Molder (Model CS-183) is set at 200° C. After the apparatus is sufficiently heated, the drive switch for the rotor is turned on and approximately 0.5 g. of the bulk powdered mixture is fed into the cup. A filament of the desired diameter (less than 1 mm. to 2 mm.) is obtained by drawing the extrudate with steady pulling; the force exerted on the hot extrudate determining the diameter of the filament. Filaments in the form of rods prepared in this way are cut in lengths of about 10 mm. having a pilocarpine content of 1.9 mg. These are tested for miotic response in the rabbit eye using the test procedure described in Example 1 with the results shown in the following table:

| Time   | Mean Pupil Diameter - mm. |                   |
|--------|---------------------------|-------------------|
| (hrs.) | Control                   | Extruded Filament |
| 0      | 7.5                       |                   |
| ½      | 7.4                       | 5.3               |
| 1½     | 7.3                       | 5.3               |
| 3½     | 7.4                       | 5.9               |
| 6      | 7.4                       | 5.5               |
| 7      | 7.5                       | 5.7               |
| 8      | 7.5                       | 6.0               |
| 9      | 7.6                       | 6.2               |

The above ophthalmic inserts are placed in a cabinet and contacted for 2 days with air at room temperature and a relative humidity of 88%. The ophthalmic inserts having an initial weight of about 18 mgs. increase to a weight of 20 mgs. in the two-day period showing a pickup of 2 mgs of water or about 11% based on the total weight of the insert. The plasticizing effect of the water makes the insert much softer and pliable.

The ophthalmic inserts can also be injection molded using the same equipment and a single or multicavity mold.

EXAMPLE 4

A mixture of 16.25 parts by weight of 60 mesh pilocarpine nitrate and 83.38 parts by weight of hydroxypropyl cellulose are thoroughly mixed and to this mixture is added 8.37 parts of propylene glycol in a high shear mixer. A small amount of resulting mixture is then compressed using the procedures described in Example 2 to form a thin solid sheet of the mixture which is cut into rectangular shaped inserts about 10 mm. by 4 mm. having a thickness of about 0.8 mm. The ophthalmic inserts containing 3.4 mg. of pilocarpine so obtained were tested in the rabbit eye for moitic response with the following results:

| Time   | Mean Pupil Diameter - mm. |                   |
|--------|---------------------------|-------------------|
| (hrs.) | Control                   | Rectangular Insert |
| 0      | 7.3                       |                   |
| ½      | 7.2                       | 4.7               |
| 1½     | 7.2                       | 4.6               |
| 3½     | 7.3                       | 4.6               |
| 6      | 7.3                       | 5.9               |
| 7      | 7.3                       | 5.9               |
| 8      | 7.3                       | 6.2               |
| 9      | 7.3                       | 6.4               |

| Time   | Mean Pupil Diameter - mm. |                    |
|--------|---------------------------|--------------------|
| (hrs.) | Control                   | Rectangular Insert |
| 10     | 7.3                       | 6.9                |

EXAMPLE 5

A mixture consisting of 17.5 parts by weight of pilocarpine alginate, 74.25 parts by weight of hydroxypropyl cellulose (KLUCEL HF), and 8.25 parts by weight of propylene glycol are mixed following the procedures described in Example 4. The resulting mixture is compressed following the procedures described in Example 2 to obtain a thin film which is cut to form rectangular inserts 10×4 mm. and about 0.8 mm. thick. These inserts containing about 2.2 mg. of pilocarpine are tested in the rabbit eye by the test procedure described in Example 1 with the following results:

| Time   | Mean Pupil Diameter - mm. |                    |
|--------|---------------------------|--------------------|
| (hrs.) | Control                   | Rectangular Insert |
| 0      | 7.3                       |                    |
| ½      | 7.3                       | 4.3                |
| 1½     | 7.3                       | 4.5                |
| 3½     | 7.3                       | 4.8                |
| 6      | 7.3                       | 5.3                |
| 7      | 7.5                       | 6.2                |
| 8      | 7.7                       | 6.9                |
| 9      | 7.5                       | 6.9                |

EXAMPLE 6

The miotic effect of a standard solution of pilocarpine and a solid pilocarpine alginate insert prepared as described by Loucas et al. are compared using the rabbit test procedure described in Example 1. In these tests dosages of 9.7 mg. of pilocarpine are used. The miotic responses are shown in the following table:

|        | Mean Pupil Diameter - mm. |                                        |                        |
|--------|---------------------------|----------------------------------------|------------------------|
| Time (hrs.) | Control              | Equivalent Dose of Pilocarpine Solution | Pilocarpine Alginate |
| 0      | 7.5                       |                                        |                        |
| ½      | 7.5                       | 4.6                                    | 4.8                    |
| 1½     | 7.5                       | 4.9                                    | 4.8                    |
| 3½     | 7.5                       | 7.2                                    | 5.3                    |
| 6      | 7.5                       | 7.4                                    | 6.6                    |
| 7      | 7.5                       | —                                      | 7.2                    |

What is claimed is:

1. The method of applying pilocarpine to the eye which comprises inserting a solid ophthalmic insert comprising between 0.1 to about 35% of pilocarpine pamoate as an ophthalmic active agent admixed in a matrix of from about 65 to about 99% of hydroxypropyl cellulose in the cul-de-sac of the conjunctiva to thereby dispense the active agent pilocarpine to the eye over a prolonged period of time.

* * * * *